United States Patent
Oguma

(10) Patent No.: US 6,818,409 B2
(45) Date of Patent: Nov. 16, 2004

(54) **ISOLATION AND PURIFICATION OF *CLOSTRIDIUM BOTULINUM* TOXINS**

(75) Inventor: Kenji Oguma, Okayama (JP)

(73) Assignees: Eisai Company Ltd., Tokyo (JP); Keiji Oguma, Okayama (JP)

( * ) Notice: Subject to any disclaimer, the term of this patent is extended or adjusted under 35 U.S.C. 154(b) by 149 days.

(21) Appl. No.: 10/137,507

(22) Filed: Apr. 30, 2002

(65) Prior Publication Data

US 2003/0008367 A1 Jan. 9, 2003

(30) Foreign Application Priority Data

Jul. 3, 2001 (JP) ........................................ 2001-202736

(51) Int. Cl.$^7$ ............................................. C07K 14/33
(52) U.S. Cl. ...................... 435/7.1; 435/7.92; 435/7.35; 435/820; 435/800; 436/516; 436/528; 530/820; 530/350; 530/412; 536/127; 514/25; 424/239.1; 424/85.1
(58) Field of Search ................................. 435/7.1, 7.92, 435/7.35, 820, 800, 193, 175, 280, 803, 825; 530/412, 350, 820; 436/516, 528; 424/239.1, 85.1, 184.1, 93.45, 247.1; 514/25; 536/127

(56) References Cited

U.S. PATENT DOCUMENTS

| | | | | | |
|---|---|---|---|---|---|
| 4,597,580 | A | * | 7/1986 | Gassie | 273/418 |
| 4,771,039 | A | * | 9/1988 | Tanaka et al. | 514/25 |
| 5,731,161 | A | * | 3/1998 | Aoki et al. | 435/7.32 |
| 6,013,634 | A | * | 1/2000 | Hindsgaul | 514/25 |
| 2004/0028703 | A1 | * | 2/2004 | Bigalke et al. | 424/239.1 |
| 2004/0071735 | A1 | * | 4/2004 | Marchini et al. | 424/239.1 |

FOREIGN PATENT DOCUMENTS

| | | |
|---|---|---|
| JP | 04154796 * 5/1992 | C07K/3/20 |
| JP | 06-192118 | 7/1994 |
| JP | 06-192296 | 7/1994 |
| WO | WO 94/00481 | 1/1994 |
| WO | WO 95/17904 | 7/1995 |
| WO | WO 95/32738 | 12/1995 |
| WO | WO 99/37326 | 7/1999 |
| WO | WO 00/69895 | 11/2000 |
| WO | WO 00/74703 A2 | 12/2000 |
| WO | WO 01/26736 A2 | 4/2001 |

OTHER PUBLICATIONS

Kouguchi, H et al, Journal of Biological Chemistry, vol. 277(4), pp. 2650–2656, Jan. 25, 2002.*

Arimitsu et al, Infection and Immunity, Mar. 2003, vol. 71(3), pp. 1599–1603.*

Inoue, K et al, Microbiology, vol. 147, pp. 811–819, 2001.*

Nilsson, UJ et al, Immobilizing of reducing sugars as toxin binding agents, Bioconjugate chemistry, vol. 8, pates 466–471, 1997.*

(List continued on next page.)

Primary Examiner—Lynette R. F. Smith
Assistant Examiner—Ginny Allen Portner
(74) Attorney, Agent, or Firm—Bell, Boyd & Lloyd LLC

(57) ABSTRACT

A method for separating and purifying HA-positive progenitor toxin(s) (LL and/or L toxins) and HA-negative progenitor toxin (M toxin) from a *Clostridium botulinum* strain is provided. The method comprises applying a liquid containing both the HA-positive progenitor toxin(s) and the HA-negative progenitor toxin to a lactose column. Also provided is a method for separating and purifying neurotoxin (7S toxin) from HA-positive progenitor toxins, which comprises treating HA-positive progenitor toxins with an alkaline buffer and then applying the resulting liquid containing dissociated neurotoxin and non-toxic components to a lactose column. Activated pure HA-positive toxins (L and LL toxins) and neurotoxin are obtained by simple procedures.

12 Claims, 6 Drawing Sheets

OTHER PUBLICATIONS

Kouguchi, H et al, European Journal of Biochemistry, vol. 268, pp. 4019–4026, FEBS 2001.*

Lamanna et al., *Botulinum* Toxin (Type A); Including A Study of Shaking with Chloroform as a step in the Isolation Procedure, J. Bacteriol., 1946, vol. 52, pp. 1–13.

Lamanna et al., *The Isolation of Type B Botulinum Toxin*, J. Bacteriol., 1947, vol. 52, pp. 575–584.

Duff et al., *Studies on Immunity to Toxins of Clostridium botulinum*, J. Bacteriol., 1957, vol. 73, pp. 42–47.

DasGupta et al., Separation of Toxin and Hemagglutinin from Crystalline Toxin of *Clostridium botulinum* Type A by Anion Exchange Chromatography and Dtermination of Their Dimensions by Gel Filtrations, J. Biol. Chem., 1968, vol. 243, pp. 1065–1072.

DasGupta et al., *A Common Subunit Structure in Clostridium botulinum Type A, B and E Toxins*, Biochem. Biophys. Res. Commun., 1972, vol. 48, pp. 108–112.

Sugii et al., *Molecular Construction of Clostridium botulinum Type A Toxins*, Infect. Immun. 1975, vol. 12, pp. 1262–1270.

Kozaki et al., *Purification and Some Properties of Progenitor Toxins of Clostridium botulinum Type B*, Infect. Immun. 1974, vol. 10, pp. 750–756.

Lacy et al., *Crystal Structure of Botulinum neurtoxin Type A and Implications for Toxicity*, Nature Structural Biol., 1988, vol. 5, pp. 898–902.

Swaminathan et al., Structural Analysis of the Catalytic and Binding Sites of *Clostridium botulinum* Neurotoxin B, Nature Structural Biol., 2000, vol. 7, pp. 693–699.

* cited by examiner

Fig. 1 Structure of *Clostridium botulinum* toxins

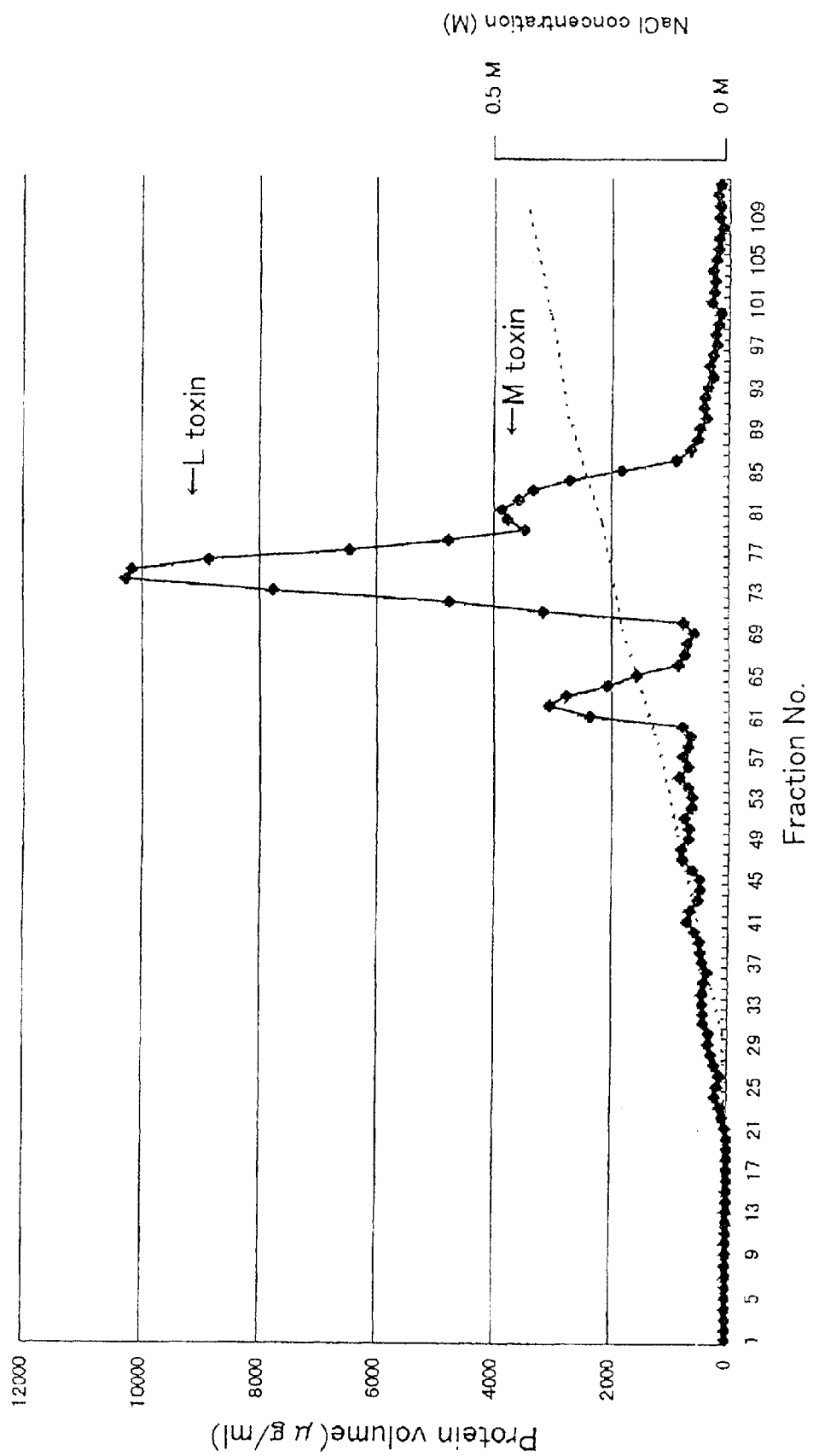
Fig. 3 Elution pattern from a SP-Toyopearl 650M ion-exchange column

Fig. 4 Separation of M and L toxins by a β-lactose column

Fig. 5 Separation of NTX from L toxin by a β-lactose column

Fig. 6

```
NTX (intact: 158kDa) →                    ← NTNH (intact: 130kDa)
NTNH (processed: 112kDa) →                ← Heavy chain of NTX (106kDa)

← HA3b (51kDa)
                                          ← Light chain of NTX (51kDa)

← HA1 (34kDa)

← HA3a (19-23kDa)

NTNH (processed: 15kDa) →                 ← HA2 (18kDa)

1   2   3   4
```

Fig. 6 Banding profiles of purified type B toxins

Lane 1, M toxin (partially nicked); 2, L toxin (partially nicked);
3, L toxin (fully nicked with trypsin); 4, NTX (fully nicked with trypsin)

US 6,818,409 B2

ISOLATION AND PURIFICATION OF CLOSTRIDIUM BOTULINUM TOXINS

BACKGROUND OF THE INVENTION

1. Field of the Invention

The present invention relates to isolation and purification of *Clostridium botulinum* toxins.

2. Description of the Prior Art

*Clostridium botulinum* strains produce seven immunologically distinct poisonous neurotoxins (NTXs, 7S toxins) and are classified into types A to G. The NTXs inhibit release of acetylcholine at the neuromuscular junctions and synapses, and cause botulism in humans and animals. All types of NTXs are synthesized as a single chain with molecular mass (Mr) of approximately 150 kDa. Endogenous protease(s) from bacteria or exogenous protease (s) such as trypsin cleave the single chain NTXs at about one third of the length from the N-terminus within a region inside a disulfide loop. NTXs therefore become dichain consisting of 50 kDa (designated as light chain) and 100 kDa (designated as heavy chain) components held together by a disulfide bond (FIGS. 1 and 6). The proteolytically processed dichain NTXs (nicked or activated form) are more potent than the single chain NTXs.

The NTXs are associated with nontoxic components in cultures or in foods, and become large complexes designated as progenitor toxins (Oguma et al., "Structure and function of *Clostridium botulinum* progenitor toxin.", J. Toxical-Toxin Reviews, 18,17–34, 1999). Type A strain produces three forms of progenitor toxins designated as LL (19S, 900 kDa), L (16S, 500 kDa), and M (12S, 300 kDa) toxins, all of which toxins are considered to be fully activated, while type B, C, and D produce two forms, L and M. Type E, F and G produce only a single form of toxin; types E and F produce M toxin, and type G produces L toxin. M toxin consists of a NTX (7S, 150 kDa) and a nontoxic component showing no hemagglutinin (HA) activity, which is described herein as non-toxic non-HA (NTNH). The molecular mass of NTNH is similar to that of NTX. L and LL toxins are formed by conjugation of M toxin with HA. HA consists of four subcomponents designated as HA1, HA2, HA3a and HA3b (FIG. 6, lanes 2 and 3). NTNH of M toxin is cleaved at its N-terminal regions, and therefore it dissociates into two bands on SDS-PAGE (112 kDa and 15 kDa in FIG. 6, lane 1). M, L and LL toxins dissociate into NTX and nontoxic components under alkaline conditions; M toxin dissociates into NTX and NTNH, and L and LL toxins dissociate into NTX and nontoxic components (NTNH+HA) which are complex of NTNH and HA (FIG. 1).

Recently, partially or almost purified type A-LL toxins and type B-L toxins have been used for the treatment of strabismus, blepharospasm, nystagmus, facial spasm, spasmodic tic, spasmodic torticollis, spastic aphonia, myokymia, bruxism, graphospasm (writer's cramp), achalasia, anismus, and many other dystonia. The toxins are now used for hidrosis and for elimination of wrinkle, also. Usually, patients are injected with these toxins at several monthintervals, and therefore a significant percentage of the patients produce a specific antibody against the injected toxin. When such anti-toxin antibody is produced in a patient, that toxin type can no longer be used for the same treatment (becomes ineffective) for the patient. It is recommended to use purified fully activated NTXs instead of L and LL toxins in order to reduce antibody production in the patients. Therefore, there has been a demand for a simple procedure to obtain each toxin type in an activated purified form, specially NTX alone.

At present, a type A-LL toxin named "BOTOX" that is partially purified from the culture supernatant by repeated precipitation with an acid (pH 5.0 to 3.7) and an alcohol (and ammonium sulfate) (Duff J T et al., "Studies on immunity to toxins of *Clostridium botulinum*. A simplified procedure for isolation of type A toxin.", J. Bacteriol. 73: 42–47, 1957) is used for the treatment of patients in need thereof. Also, type A-LL toxin and type B-L toxin named "DYSPORT" and "MYOBLOC", respectively, have been used. Detailed procedure for purifying these preparations is not clear. However, it is reported that molecular mass of MYOBLOC is 700 kDa and the specific activity of this toxin is relatively low because some of the toxin may be in an un-nicked (un-activated) form. The molecular mass of purified type B-L and -M toxins is reported as 500 and 300 kDa, respectively. Therefore, a 700 kDa preparation seems to be somewhat different from the purified L and M toxins.

The procedure for purifying the type B-L and-M toxins and TX reported by Kozaki, Sakaguchi, and Sakaguchi is as follows: The organisms were incubated in peptone-yeast extract-glucose (PYG) medium at 30° C. for 4 days. The precipitate formed by adding 3 N sulfuric acid to pH 4.0 was collected by centrifugation, and the toxins were extracted with 0.2 M phosphate buffer, pH 6.0. The toxins were again precipitated at 20% and then 60% saturation of ammonium sulfate, and the precipitate was dissolved in the same buffer. After treating the extract with ribonuclease, the preparation was adjusted to pH 4.2 with 1 M acetic acid and dialyzed against 0.05 M acetate buffer, pH 4.2. A white precipitate which appeared was collected by centrifugation, washed and then resuspended in 0.05 M acetate buffer, pH 4.2, containing 0.5 M NaCl. This preparation was then treated with protamine (0.06%), and centrifuged. The supernatant was percolated through a sulphopropyl (SP)-Sephadex column equilibrated with 0.05 M acetate buffer containing 0.5 M NaCl to remove the excess protamine. The column effluent was diluted with the 0.05 M acetate buffer to lower the NaCl concentration to 0.2 M, and then applied to a SP-Sephadex column equilibrated with the same buffer with 0.2 M NaCl. The toxin, adsorbed onto the column, was eluted with a linear gradient of NaCl from 0.2 to 0.4 M in the same buffer. The toxic fractions were pooled and concentrated by ultrafiltration, and then applied to a Sephadex G-200 column equilibrated with the same buffer with 0.5 M NaCl. The L and M toxins were obtained separately. From these L and M toxins, NTX was obtained by applying them to a DEAE-Sephadex A-50 column equilibrated with 0.01 M phosphate buffer, pH 8.0. "(Kozaki S., Sakaguchi S. and Sakaguchi G. Purification and some properties of progenitor toxins of *Clostridium botulinum* type B. Infect. Immun. 10: 750–756, 1974).

However, conventional purification procedures are very complicated and recovery of toxins is not high. In some strains of types B, C, D and F, fully activated toxins have not been obtained.

SUMMARY OF THE INVENTION

An object of the invention is to provide a method for obtaining purified activated toxins in a simple manner.

We have found that hemagglutinin (HA) specifically binds to lactose. Based on this finding, we have developed simple procedures for separating HA-positive and HA-negative progenitor toxins from each other, and also for separating and purifying NTXs from HA-positive progenitor toxins. Furthermore, we have found that if HA-positive progenitor toxins are first treated with trypsin and then applied to a β-lactose column, fully activated HA-positive progenitor toxins that contain little trypsin can be obtained.

Thus, according to the present invention, there is provide a method for separating and purifying HA-positive progenitor toxin(s) (LL and/or L toxins) and HA-negative progenitor toxin (M toxin) from a *Clostridium botulinum* strain, which comprises applying a liquid containing the HA-positive progenitor toxin(s) and the HA-negative progenitor toxin to a lactose gel column preferably under an acid condition.

There is also provide a method for separating and purifying neurotoxin (7S toxin) from HA-positive progenitor toxins (L and/or LL toxins), which comprises treating the HA-positive progenitor toxins from a *Clostridium botulinum* strain with an alkaline buffer to dissociate the progenitor toxins into neurotoxin and non-toxic components, and then applying the resulting liquid containing the neurotoxin and the non-toxic components to a lactose gel column.

BRIEF EXPLANATION OF DRAWINGS

Figure 1:
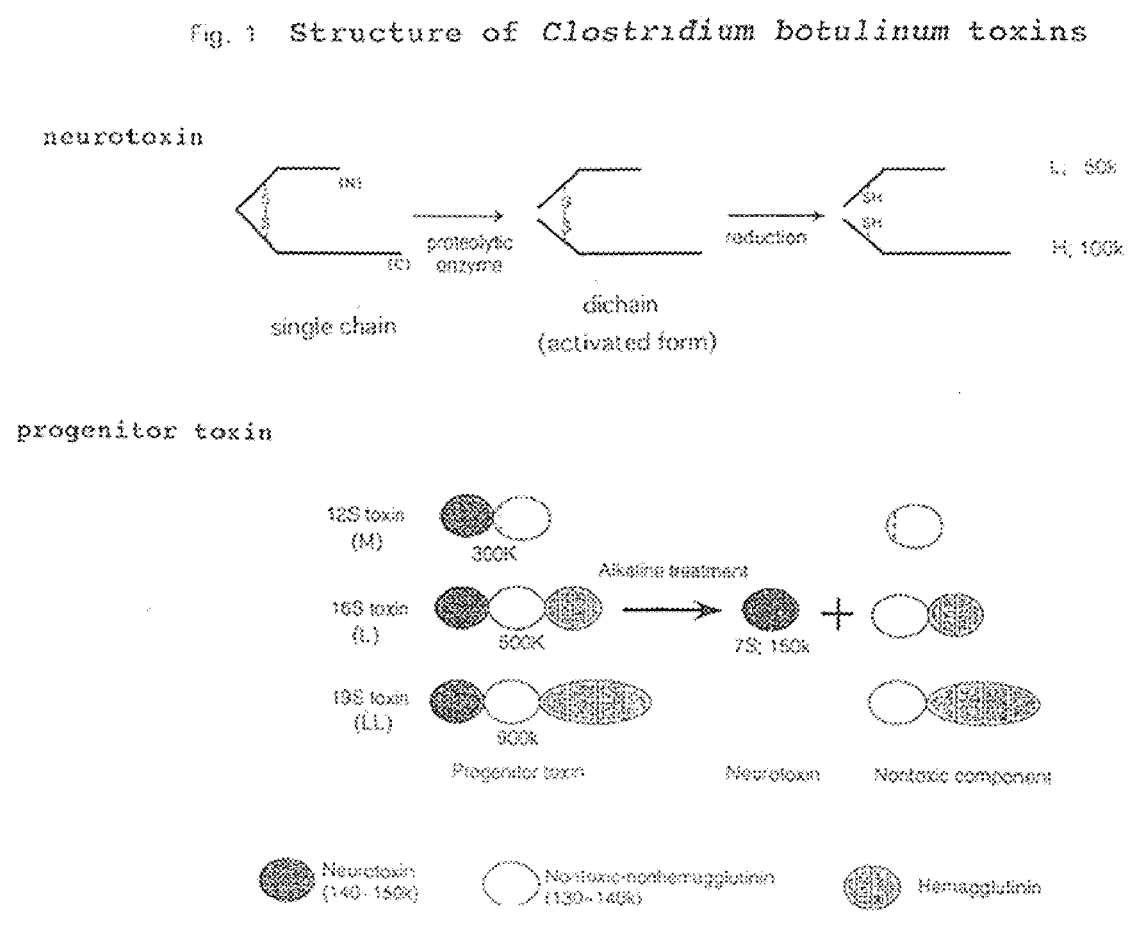

FIG. 1 shows structures of *Clostridium botulinum* toxins;

FIG. 3 is a graph showing the elution pattern of a sample containing M toxin and L toxin from an ion exchange column;

FIG. 4 is a graph showing OD values of M toxin and L toxin separated by a β-lactose column: and FIG. 5 is a graph showing OD values of NTX and non-toxic components separated by a β-lactose column.

FIG. 6 is a picture showing banding profiles of purified type B preparations on SDS-PAGE.

DESCRIPTION OF PREFERRED EMBODIMENTS

Neurotoxin (NTX) and Progenitor Toxin

Figure 2:
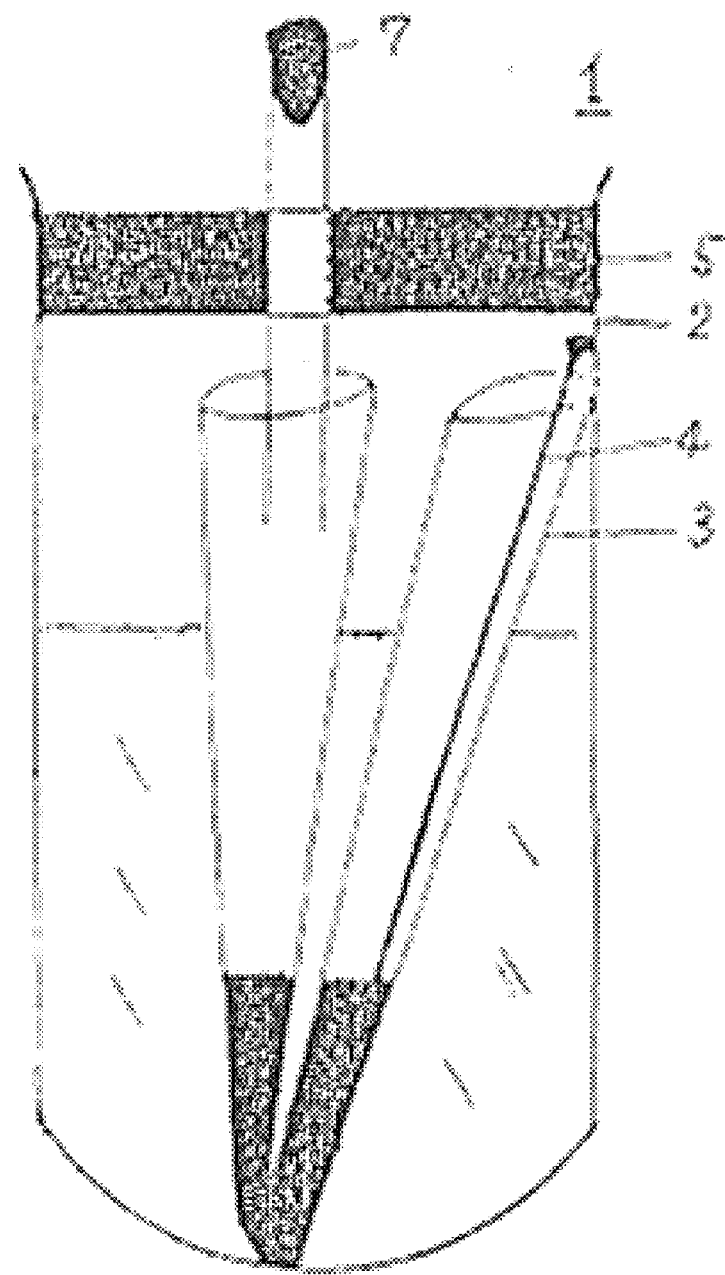
FIG. 2 shows a device used for a cellophane tube procedure.

The NTX means 7S toxin having a molecular mass of 150 kDa.

The progenitor toxin means M toxin (12 S toxin, 300 kDa), L toxin (16 S toxin, 500 kDa) and LL toxin (19 S toxin, 900 kDa), all of which contain 7S toxin and non-toxic components.

The progenitor toxins can be separated into two groups, HA-positive (L and LL) toxins and HA-negative (M) toxin. The L and LL toxins contain both the HA and non-HA (NTNH) as the non-toxic components, while the M toxin contains only the non-toxic non-HA (NTNH) as the non-toxic component.

Incidentally, neurotoxin (NTX) may be included in HA-negative toxins.

*Clostridium botulinum* Strains

The *Clostridium botulinum* strains to which the method of the present invention is applicable include HA-positive (L and LL) toxins and HA-negative (M, 7S) toxins. These strains can be classified into *Clostridium botulinum* types A, B, C, and D (probably G, also). Type B strain is preferably used in the present invention.

Lactose Column

The lactose column is preferably a beta (β)-lactose gel column such as one in which β-lactose gel available from E-Y Laboratories Inc. (Sanmated Calif., USA) is packed in a small glass column.

Procedures

Specifically, the method of the invention can be carried out as follows:

I. Separation of HA-positive and HA-negative progenitor toxins

1) A *Clostridium botulinum* strain is incubated by a cellophane tube procedure, and toxins (including HA-positive and HA-negative progenitor toxins) are precipitated with ammonium sulfate. The resulting precipitate is dialyzed against a phosphate buffer with an acid pH (usually pH 6.0).

2) The resulting sample is then reacted with protamine. After centrifugation, the supernant is dialyzed against a 0.05M sodium acetate buffer (pH 4.2), and then layered on an ion exchange column, and the fractions of HA-positive and HA-negative progenitor toxins eluted from this column are pooled.

3) The pooled preparations are preferably treated with trypsin at a pH in a range of about 5.5 to 6.5, preferably at about pH 6.0, and then applied to a β-lactose gel column equilibrated with 0.01M phosphate buffer under an acid condition usually at pH 6.0.

4) HA-negative toxin appears in the flow-through fractions, while HA-positive toxins are bound to the column. After washing the column, the HA-positive toxins are eluted with the same buffer containing 0.2 M lactose to give purified HA-positive toxins.

II. Purification of NTX from HA-positive progenitor toxins

1) The HA-positive toxins thus obtained are dialyzed against a buffer with an alkaline pH in order to dissociate the HA-positive toxins into NTX and nontoxic components (HA+NTNH), and then applied to a β-lactose gel column equilibrated with the same buffer. The nontoxic components are bound to the column, whereas the NTX is contained in the flow-through fractions. The buffer used herein is preferably 0.01M phosphate buffer having a pH in the range of from 7.5 to 9.0, more preferably from 7.5 to 8.5, particularly about 8.0.

2) The bound nontoxic components are eluted by a buffer containing a lactose.

The invention will be explained in detail by way of the following examples.

EXAMPLE 1

Separation and Purification of M Toxin and L Toxin

*Clostridium botulinum* strain of type B was cultured at 35° C. for 5 days by a cellophane tube procedure similar to the procedure reported by Stern and Wentzel (Stern M, Wentzel L M. "A new method for the large scale production of high titer botulinum formol-toxoid types C and D.", J. Immunol. 65: 175–183, 1950 3) using a dialysis tube device 1 (FIG. 2). The device includes glass container 2, dialysis tube 3 placed in the glass container 2, glass rod 4 placed in the dialysis tube 3, rubber stopper 5, glass tube 6 and cotton plug 7. The dialysis tube 3 is charged with an aqueous solution containing 10% by weight of glucose, 5% by weight of NaCl and 1% by weight of cystein-HCl. In the glass container 2 and outside of the dialysis tube 3 is placed a solution containing 2% by weight of polypeptone, 2% by weight of lactoalbumin hydrolysate, 1% by weight of peptone and 1% by weight of yeast extract.

The cells and toxins were collected from the cellophane tube and centrifuged at 15,000 g for 30 minutes. The toxins in the supernatant were precipitated with a 60% saturated ammonium sulfate. After centrifugation at 15,000 g for 20 minutes, the precipitate was resuspended into a 0.05 M phosphate buffer with pH 6.0, dialyzed against the same buffer, and then treated with protamine (final concentration 0.4%) to remove RNA. After centrifugation at 15,000 g for 20 minutes, the supernatant was dialyzed against 0.05 M sodium acetate buffer(pH 4.2), and then layered on a cation exchange resin column, SP-Toyopearl 650M (tradename, Tosoh Chemical, Tokyo, Japan), equilibrated with the same buffer. The M and L toxins were eluted by an exponential gradient of NaCl (0 to 0.5 M) in the same buffer (FIG. 3). The fractions of M and L toxin were pooled, dialyzed against 0.01 M phosphate buffer(pH 6.0), followed by trypsin treatment in the same buffer at 37° C. for 30 minutes. The level of toxin activation was increased approximately 10 fold by the trypsin treatment.

Figure 4:
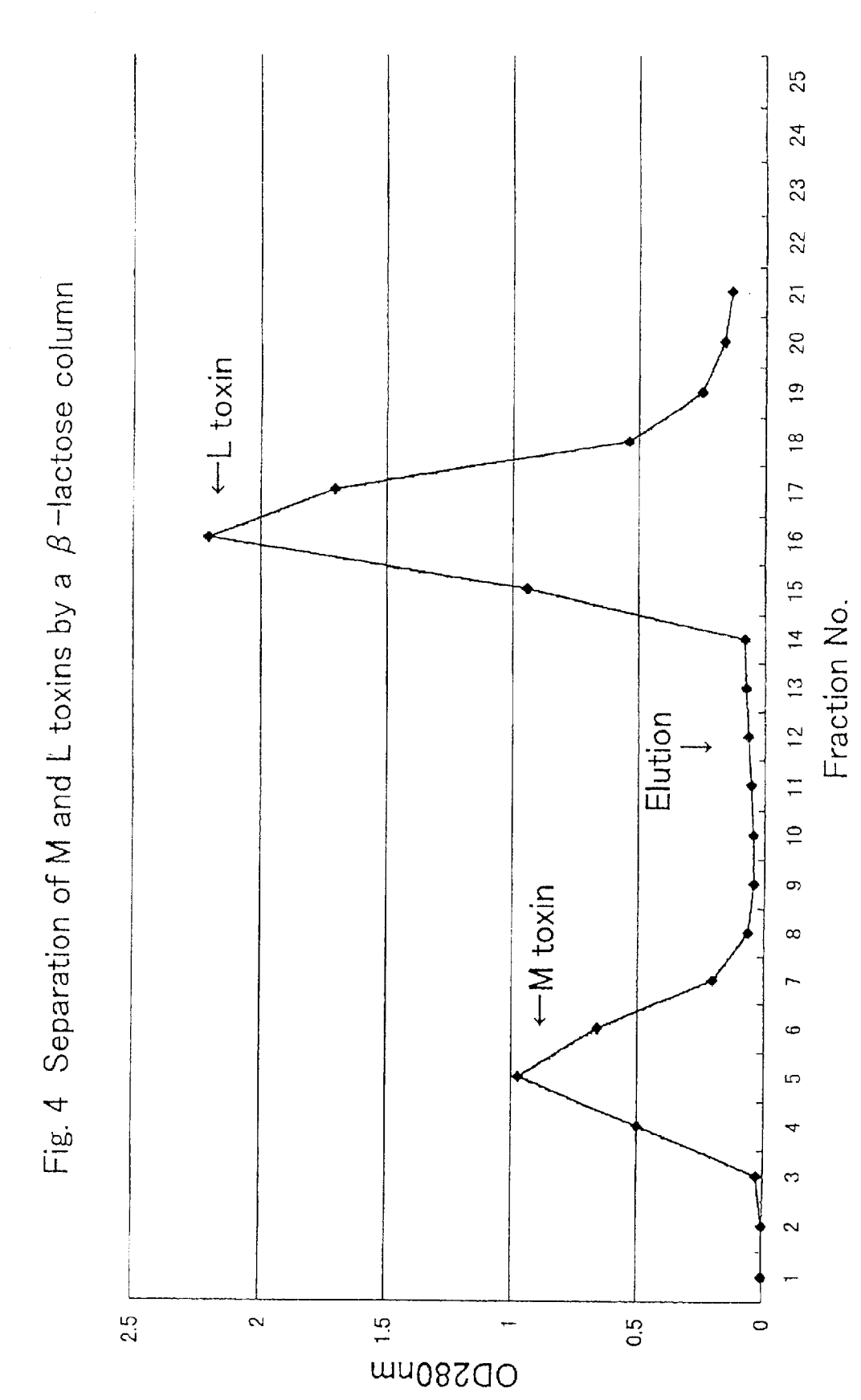

A 5 ml portion of β-lactose gel (purchased from E-Y Laboratories) was packed in a column (1×6 cm) and equilibrated with a 0.01 M phosphate buffer (pH 6.0). The activated M and L toxins obtained in the above were then applied to the β-lactose gel column. The M toxin was obtained in the flow-through fraction, while the L toxin was bound to the column. After washing out the M toxin and trypsin, the L toxin was eluted with the same buffer containing 0.2 M lactose (FIG. 4). Purity of each of the M and L toxins thus obtained was assayed by sodium dodecyl sulfate-polyacrylamide gel electrophoresis (SDS-PAGE) stained with Coomassie brilliant blue (FIG. 6). Based on the banding profiles, it was found that the preparation each of M and L toxins scarcely contained contaminants (FIG. 6, lanes 1 and 2). The recovery of the M and L toxins from the β-lactose gel column was approximately 80%.

EXAMPLE 2

Separation and Purification of NTX

Figure 5:
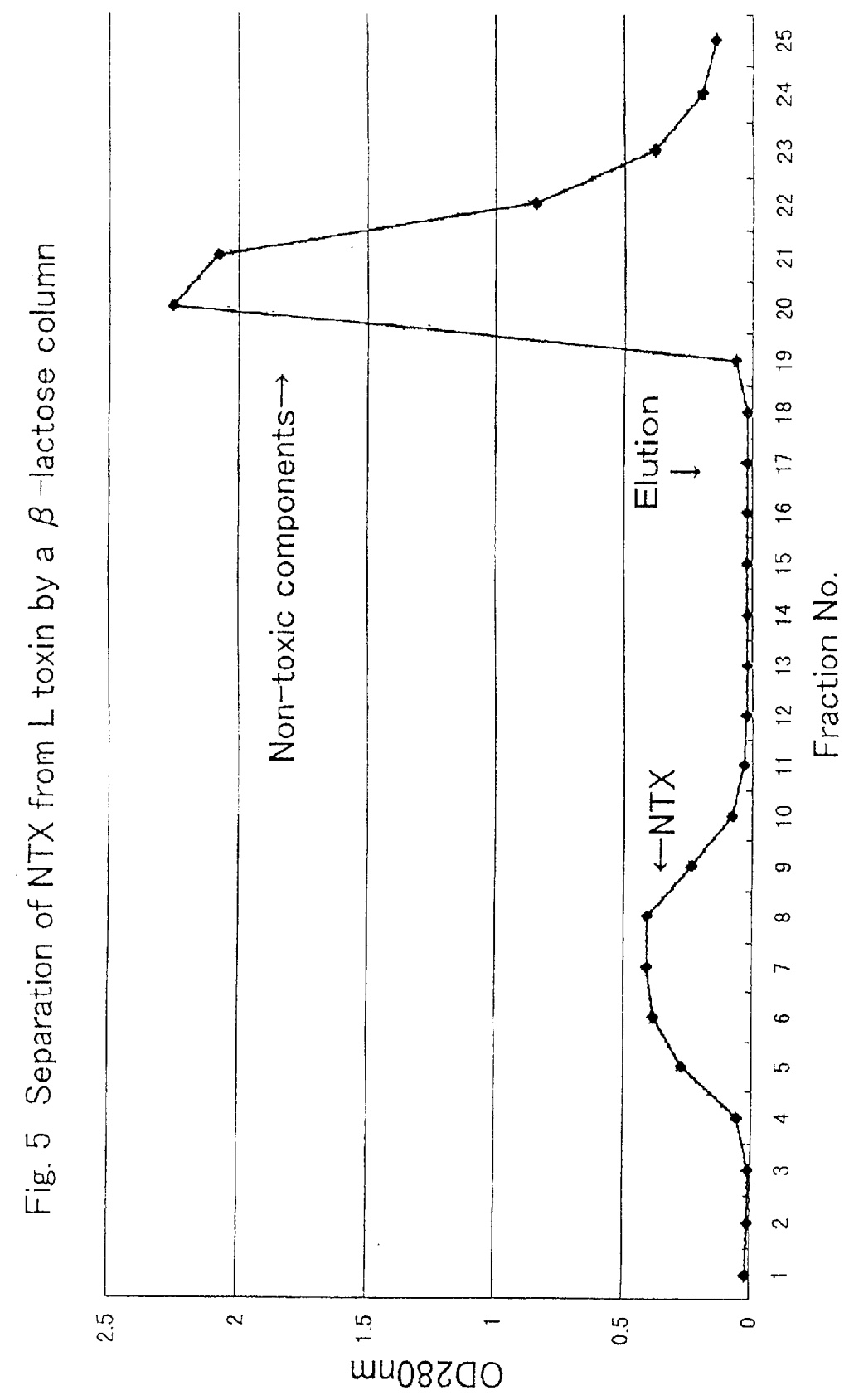

The purified activated L toxin obtained in Example 1 was dialyzed against a 0.01 M phosphate buffer (pH 8.0), and then applied to the β-lactose gel column (which had been prepared as in Example 1) equilibrated with the same buffer. The NTX was obtained in the flow-through fractions (FIG. 5). Recovery of NTX from the L toxin was more than 80%. Purity of the NTX thus obtained was assayed by SDS-PAGE stained with Coomassie brilliant blue. Based on the banding profiles, it was found that the purity of the NTX was about 100%, although several faint bands made by processing of the toxins (NTX and L toxin) with trypsin were demonstrated in some preparations (FIG. 6, lanes 3 and 4).

According to the present invention, HA-positive toxins (L and LL toxins) and HA-negative toxin (M toxin) can be separated by a simple operation. In addition, fully activated pure NTXs can be obtained from the HA-positive toxins. The resulting HA-positive toxins and NTXs contain neither trypsin nor any contaminants harmful to humans.

What is claimed is:

1. A method for separating and purifying one or more hemagglutinin (HA)-positive progenitor toxins including at least one of an LL toxin and an L toxin and at least one HA-negative progenitor toxin including an M toxin derived from a *Clostridium botulinum* strain, which comprises applying a liquid containing both the HA-positive progenitor toxins and the HA-negative progenitor toxin to a lactose column under an acid condition thereby separating and purifying the HA-positive progenitor toxins and the HA-negative progenitor toxin.

2. The method according to claim 1, wherein the lactose column is a β-lactose gel column.

3. The method according to claim 1, wherein the HA-positive progenitor toxins and HA-negative progenitor toxin are type B toxins.

4. The method according to claim 2, wherein the HA-positive progenitor toxins and HA-negative progenitor toxin are type B toxins.

5. The method according to claim 1 further comprising the step of treating the progenitor toxins in the liquid with trypsin, wherein the liquid containing the HA-positive progenitor toxins and the HA-negative progenitor toxin is treated with trypsin to activate the progenitor toxins before applying to the lactose column.

6. The method according to claim 2 further comprising the step of treating the progenitor toxins in the liquid with trypsin, wherein the liquid containing the HA-positive progenitor toxins and the HA-negative progenitor toxin is treated with trypsin to activate the progenitor toxins before applying to the lactose column.

7. A method for separating and purifying a neurotoxin including a 7S toxin derived from one or more hemagglutinin (HA)-positive progenitor toxins including at least one of an L toxin and an LL toxin which comprises treating the HA-positive progenitor toxins from a *Clostridium botulinum* strain with an alkaline buffer to dissociate the progenitor toxins into the neurotoxin and one or more non-toxic components, and then applying the resulting liquid containing the neurotoxin and the non-toxic components to a lactose column under an alkaline condition, thereby separating and purifying a neurotoxin from the HA-positive progenitor toxins.

8. The method according to claim 7, wherein the lactose column is a β-lactose gel column.

9. The method according to claim, 7, wherein the HA-positive progenitor toxins are type B toxins.

10. The method according to claim 8, wherein the HA-positive progenitor toxins are type B toxins.

11. The method according to claim 7, further comprising the step of treating the progenitor toxins in the liquid with trypsin, wherein the HA-positive progenitor toxins are activated HA-positive progenitor toxins by the treatment with trypsin.

12. The method according to claim 8, further comprising the step of treating the progenitor toxins in the liquid with trypsin, wherein the HA-positive progenitor toxins are activated HA-positive progenitor toxins by the treatment with trypsin.

* * * * *